(12) United States Patent
Schierholz

(10) Patent No.: US 11,185,616 B2
(45) Date of Patent: Nov. 30, 2021

(54) IMPLANTABLE MEDICAL PRODUCTS, A PROCESS FOR THE PREPARATION THEREOF, AND USE THEREOF

(71) Applicant: Jörg Michael Schierholz, Starnberg-Bete (DE)

(72) Inventor: Jörg Michael Schierholz, Starnberg-Bete (DE)

(73) Assignee: Jörg Michael Schierholz, Starnberg-Bete (DE)

( * ) Notice: Subject to any disclaimer, the term of this patent is extended or adjusted under 35 U.S.C. 154(b) by 0 days.

(21) Appl. No.: 16/074,134

(22) PCT Filed: Jan. 31, 2017

(86) PCT No.: PCT/EP2017/052040
§ 371 (c)(1),
(2) Date: Jul. 31, 2018

(87) PCT Pub. No.: WO2017/134049
PCT Pub. Date: Aug. 10, 2017

(65) Prior Publication Data
US 2019/0167859 A1 Jun. 6, 2019

(30) Foreign Application Priority Data
Feb. 1, 2016 (EP) .................................. 16153686

(51) Int. Cl.
*A61L 31/16* (2006.01)
*A61L 31/06* (2006.01)
(Continued)

(52) U.S. Cl.
CPC .......... *A61L 31/16* (2013.01); *A61K 31/4174* (2013.01); *A61K 31/444* (2013.01);
(Continued)

(58) Field of Classification Search
CPC .............. A61K 31/496; A61K 31/4174; A61L 2300/42; A61L 2300/424; A61L 2300/404; A61L 2420/02
See application file for complete search history.

(56) References Cited

U.S. PATENT DOCUMENTS

| 4,612,337 A | 9/1986 | Fox, Jr. et al. |
| 4,642,104 A | 2/1987 | Sakamoto et al. |
(Continued)

FOREIGN PATENT DOCUMENTS

| DE | 3613213 A1 | 10/1987 |
| DE | 3725728 A1 | 2/1989 |
(Continued)

OTHER PUBLICATIONS

Hanada et al., Miconazole as Inflammatory Agent. II: Time Course of Pleurisy and Drug Interference. Gen Pharmacol.; 30(5): 791-4 (1998). (Abstract Only).

(Continued)

*Primary Examiner* — Jianfeng Song
(74) *Attorney, Agent, or Firm* — Christensen Fonder Dardi; Andrew H. Auderieth; Peter S. Dardi

(57) ABSTRACT

Implantable medical product, comprising a basic body and an imidazole derivative in the form of its free base;
wherein said basic body has on its polymeric surface a layer containing the imidazole derivative as an active ingredient, which displays an antithrombogenic, antiproliferative, anti-inflammatory or antiadhesive effect, or a combination thereof.

16 Claims, 1 Drawing Sheet

(51) Int. Cl.
| | |
|---|---|
| A61L 29/06 | (2006.01) |
| A61L 31/10 | (2006.01) |
| A61L 29/16 | (2006.01) |
| A61K 31/444 | (2006.01) |
| A61K 31/4174 | (2006.01) |
| A61K 31/496 | (2006.01) |
| A61K 31/573 | (2006.01) |
| A61L 33/00 | (2006.01) |
| A61L 33/04 | (2006.01) |
| A61L 27/34 | (2006.01) |
| A61L 29/10 | (2006.01) |
| A61L 27/54 | (2006.01) |

(52) U.S. Cl.
CPC .......... *A61K 31/496* (2013.01); *A61K 31/573* (2013.01); *A61L 27/34* (2013.01); *A61L 27/54* (2013.01); *A61L 29/06* (2013.01); *A61L 29/10* (2013.01); *A61L 29/16* (2013.01); *A61L 31/06* (2013.01); *A61L 31/10* (2013.01); *A61L 33/0041* (2013.01); *A61L 33/04* (2013.01); *A61L 2300/216* (2013.01); *A61L 2300/404* (2013.01); *A61L 2300/406* (2013.01); *A61L 2300/41* (2013.01); *A61L 2300/416* (2013.01); *A61L 2300/42* (2013.01); *A61L 2300/424* (2013.01); *A61L 2420/02* (2013.01)

(56) References Cited

U.S. PATENT DOCUMENTS

| | | | |
|---|---|---|---|
| 4,677,143 A | 6/1987 | Laurin et al. | |
| 4,713,239 A | 12/1987 | Babaian et al. | |
| 4,999,210 A | 3/1991 | Solomon et al. | |
| 5,451,424 A | 9/1995 | Solomon et al. | |
| 5,525,348 A | 6/1996 | Whitbourne et al. | |
| 5,688,516 A | 11/1997 | Raad et al. | |
| 6,224,579 B1 * | 5/2001 | Modak | A01N 59/16 424/422 |
| 8,877,882 B1 | 11/2014 | Salamone et al. | |
| 2007/0225800 A1 * | 9/2007 | Sahatjian | A61F 2/91 623/1.42 |
| 2013/0158488 A1 * | 6/2013 | Weaver | A61M 25/0043 604/264 |

FOREIGN PATENT DOCUMENTS

| | | |
|---|---|---|
| EP | 0328421 A2 | 8/1989 |
| EP | 0350161 A2 | 1/1990 |
| EP | 0231573 B1 | 11/1991 |
| EP | 0301717 B1 | 11/1991 |
| EP | 0470443 B1 | 2/1992 |
| EP | 0484057 A2 | 5/1992 |
| EP | 0520160 A1 | 12/1992 |
| EP | 0640661 | 3/1995 |
| WO | 87-01595 | 3/1987 |
| WO | 87-03495 | 6/1987 |
| WO | 89-04628 | 6/1989 |
| WO | 89-09626 | 10/1989 |
| WO | 92-01542 A2 | 2/1992 |
| WO | 95-04568 | 2/1994 |
| WO | 94-10838 | 5/1994 |
| WO | 96-32907 | 10/1996 |
| WO | 96-33670 | 10/1996 |
| WO | 96-39200 | 12/1996 |
| WO | 96-39215 | 12/1996 |
| WO | 97-25085 | 7/1997 |
| WO | 00-07574 | 2/2000 |
| WO | 2016-014119 A1 | 1/2016 |

OTHER PUBLICATIONS

Helmeste et al., "Inhibition of Platelet Serotonin Uptake by Cytochrome P450 Inhibitors Miconazole and Econazole", Life Sciences, vol. 62, Issue 24, Ph. 2203-2208, May 8, 1998. (Abstract Only).

Ishikawa et al., "Miconazole Inhibition of Platelet Aggregation by Inhibiting Cyclooxygenase," Biochem Pharmacol, 35(11) 1787-92, Jun. 1986. (Abstract Only).

Köfeler et al., "Effect of cytochrome P-450 inhibitors econazole, bifonazole and clotrimazole on prostanoid formation", British Journal of Pharmacology (2000) 130, 1241-1246.

Mertens et al., A Double-Blind Study Comparing Daktacort, Miconazole and Hydrocortisone in Inflammatory Skin Infections. Dermatologica. 153(4): 228-35, (1976). (Abstract Only).

Needleman et al. "Application of Imidazole as a Selective Inhibitor of Thromboxane Synthetase in Human Platelet", Proc. Natl. Acad. Sci. USA, vol. 74, No. 4, pp. 1716-1720 (1997).

Riley et al., "A Large Randomized Clinical Trial of a Silver-Impregnated Urinary Catheter: Lack of Efficacy and Staphylococcal Superinfection", Am J Med, 98(4): 349-56, Apr. 1995. (Absract Only).

Steinhilber et al. Effects of Novel Antifungal Azole Derivatives on the 5-Lipoxygenase and Cyclooxygenase Pathway. Arzneimittelforschung; 40(11): 1260-3. (1990). (Abstract Only).

\* cited by examiner

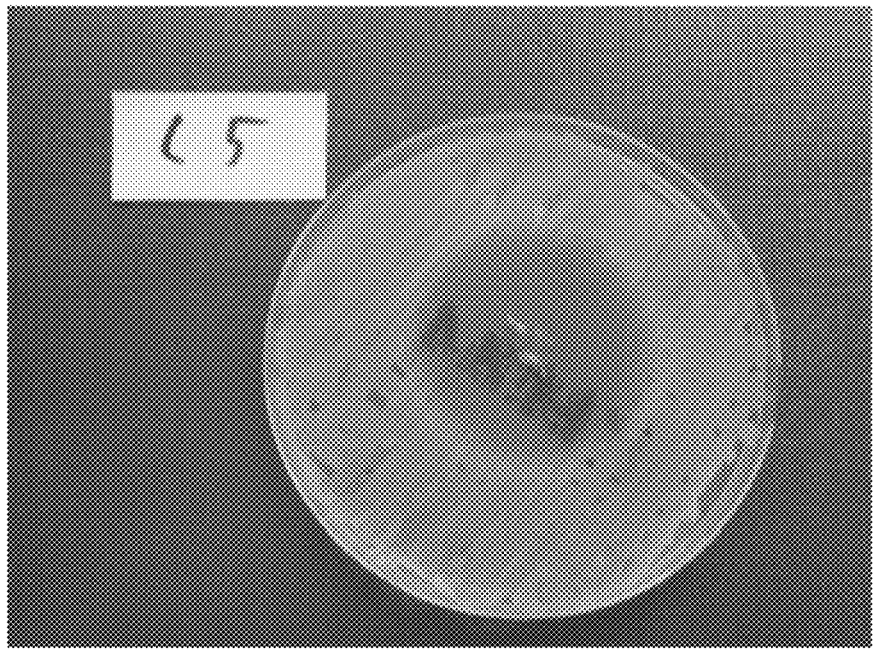

IMPLANTABLE MEDICAL PRODUCTS, A PROCESS FOR THE PREPARATION THEREOF, AND USE THEREOF

CROSS REFERENCE TO RELATED APPLICATIONS

This application is a National Stage filing of PCT Application No.: PCT/EP2017/052040, filed Jan. 31, 2017, which claims priority to European Patent Application No.: 16153686.7, filed Feb. 1, 2016, both of which are incorporated herein by reference.

The present invention relates to implantable medical products, the preparation thereof, and the use of imidazole derivatives in implantable medical products.

"Medical product" relates to an object or substance that is used for medical-therapeutic or diagnostic purposes, wherein the intended main effect is mostly a physical or physicochemical one. However, this main effect may be supported by substances that are, for example, metabolically, pharmacologically or immunologically effective.

Various compositions are known from the prior art as materials used in medical products.

WO 00/07574 discloses medical products with retarded pharmacological activity, and processes for the preparation thereof. It preferably employs salts for treating the medical products in order to achieve the desired properties.

DE 36 13 213 A1 discloses an absorbable porous tricalcium phosphate with a mixture of an antibiotic and another filler, especially a hydrophilic amino acid, as being particularly advantageous for the preparation of bone cements. A low-molecular weight additive is incorporated in the tricalcium phosphate: glycine, which is water-soluble and accelerates the release of the active ingredient from the porous tricalcium phosphate.

WO 89/09626 discloses a hydrogel coated flexible tube which is loaded with polymyxin and which is intended to prevent that polymyxin-sensitive microorganisms form thrombi or induce an infection.

U.S. Pat. No. 4,612,337 describes a method in which plastic materials are soaked in solutions of organic solvents containing various active substances, for example, ethanol, chloroform, are surface-coated after drying, and induce a short-term release of the active substance.

EP 0 520 160 A1 describes the swelling of polyurethane catheters with fluorinated hydrocarbons in which quaternary ammonium salts are incorporated by such process. After drying, the catheters are intended to become antimicrobially active through release.

DE 37 25 728 A1 describes a method in which silver metal ions are added to polyurethane/silicone mixtures. Through the mixing of polyurethanes with silicone, body fluid is supposed to penetrate in the mixture of plastics and thus wash out the silver ions, which is supposed to have an improved germicidal effect.

WO 89/04628 discloses the treatment of silicone implants with antibiotics and chloroform such that the active substances can diffuse into the outer layers of the implant material, and thus a short-time release of active substances is provided after the implantation of the finished device.

WO 87/03495 describes exactly the same method as WO 89/04628, with a drawing illustrating how catheters can be impregnated.

EP 0 484 057 A2 describes an aqueous coating for rendering medical products antithrombogenic by mixing organic polymers, binders, spacers and heparin as the antithrombogenic agent with methylene/acrylic acid copolymer and colloidal silicates. This resin may also be preliminarily sulfonated before this resin coating is applied to the medical products.

U.S. Pat. No. 4,642,104 discloses a urethral catheter made of an olefinic polymer or a silicone material in which antimicrobial substances are bound on the outside and inside.

U.S. Pat. No. 4,677,143 describes antimicrobial mixtures for coating medical products. These mixtures consist of acrylonitrile block polymers, polyvinyl chloride, mixtures of polyesters and polyurethanes, styrene block copolymers and natural rubbers and polycarbonates, nylon and silicone materials which are mixed with oligodynamic substances, i.e., antibacterial metals, preferably silver oxide compounds. These catheters were examined in a clinical test with 1,300 patients. No difference as compared to uncoated catheters was found (Riley et al., 1995, Am. J. Med.).

WO 87/01595 discloses how antimicrobially active substances, antibiotics, are added to plastic materials prior to the chemical polymerization process. The active substance is uniformly distributed in the plastic material prior to polymerization. Application example: external fixer.

WO 95/04568 describes injection ports which include antimicrobial substances, for example, chlorhexidine, silver sulfadiazine, and others.

U.S. Pat. No. 5,525,348 discloses coatings with polyvinylpyrrolidone in different solvents, followed by the addition of various other oligomers with heparin benzalkonium chloride which yield ionic surfactant coatings.

EP 0 640 661 A2 describes mixtures of silicone with silver-containing zeolites, the silver ions diffusing out of these zeolites.

EP 0 301 717 B1 also describes zeolites which are incorporated in medical plastics. These zeolites comprise silver, copper or zinc which are incorporated by kneading and are supposed to achieve the antimicrobial effect.

EP 0 470 443 B1 discloses how thin coatings are applied, for example, to catheter materials at low extrusion temperatures together with temperature-sensitive pharmaceutical ingredients.

U.S. Pat. No. 5,451,424 describes lamination processes via the extrusion of plastics by which medical products are coated with medicaments on the outside and inside thereof.

WO 92/01542 describes how coatings for nasoootopharyngial tubes are prepared by "solvent casting", i.e., immersing the medical products in a solution of plastics in which medicaments are dissolved, for example, in order to prevent chronic infections and inflammations of the surrounding tissue.

WO 96/39200 describes that a metal salt can be incorporated in a plastic matrix by "solvent casting".

U.S. Pat. No. 4,999,210 describes how a homogeneous melt of plastics and chlorhexidine is prepared, and the mixture is coextruded onto medical articles through a twin-screw compounder. These articles are later again placed in a dipping solution (solvent casting) with a hydrophilic polymer.

EP 0 350 161 A2 discloses how a substrate is coated with an ammonium salt and then heparinized at an alkaline pH value.

EP 0 231 573 B1 describes that pharmaceutical substances are incorporated in solid plastics by either solvent casting or adsorption by swelling.

WO 96/32907 describes a metallic stent with a hydrophobic elastomeric plastic layer in which a biologically active substance is incorporated. The method involves "solvent casting". Heparin is preferably used at a weight proportion of from 10 to 45%, with a layer thickness of between 30 and 150 μm, and dexamethasone with a proportion of between 0.5 and 10%.

WO 96/39215 describes how a silicone flexible tube is produced which has a layer with pharmacologically active substances inside the material which slowly diffuse outwards through the uncoated outside layer. A sandwich catheter is produced using a silicone extrusion machine. Rifampicin and minocyclin are introduced in the intermediate layer as powders.

WO 96/33670 discloses how antimicrobial mixtures, preferably rifampicin/minocyclin mixtures, are incorporated in medical plastics by swelling and increasing the temperature followed by alkalizing the solution.

WO 94/10838 describes solutions with minocyclin-EDTA with which medical products are rinsed in order to prevent infections.

U.S. Pat. No. 5,688,516 describes mixtures of pharmaceutical substances which are intended to contain the three above mentioned groups of active substances, i.e., anticoagulants, antithrombotics and complexing agents, such as EDTA or DMSA. These active substances are to be applied to medical products precoated with TDMAC.

WO 97/25085 relates to medical products containing triclosane.

U.S. Pat. No. 4,713,239 relates to a medical product consisting of a support material which is a homopolymer of acrylamide or vinyl pyrrolidone or a copolymer thereof with acrylate containing from 99 to 70% of acrylamide with vinyl pyrrolidone and from 1 to 30% by weight of acrylate having a molecular weight of from 50,000 to 1,000,000, and an active ingredient having antianginal activity, the components being contained in the following amounts: active ingredient having antianginal activity: from 3 to 30% by weight; biologically soluble and absorbable support: from 70 to 97% by weight.

EP 0 328 421 A1 relates to an infection-resistant composition, medical products and surfaces, and methods for the preparation and use thereof. The infection-resistant medical product disclosed therein comprises one or more matrix-forming polymers selected from the group consisting of biomedical polyurethanes, biomedical silicones and biodegradable polymers, and antimicrobial agents, especially a synergistic combination of a silver salt and chlorhexidine, or a salt thereof. Also disclosed are medical products having synergistic compositions therein or on the surface thereof.

WO2016/014119A1 discloses non-antigenic, resilient, bioremodelable, biocompatible tissue prostheses that can be engineered into a variety of shapes and used to repair, augment, reconstruct or replace damaged or diseased biological structures and associated tissue.

U.S. Pat. No. 8,877,882 B1 discloses liquid adhesive coating materials which are prepared that protect surfaces, such as medical devices and biological surfaces, including skin and mucous membranes, from pressure, shear and friction. The liquid coating materials utilize an amphiphilic siloxysilane/hydroxyalkyl ester polymer-containing coating material dissolved in a volatile solvent, with or without an antimicrobial agent, where when the polymer coating is formed after solvent evaporation and is folded against itself or placed against another material, the surface of said coating does not adhere, while the bottom of the coating remains attached to the original surface.

Although a wide variety of approaches for optimizing the surfaces of medical products has been known, alternative and, in the ideal case, improved medical products are needed.

The object of the present invention is to provide a medical product that reduces or prevents the adhesion of body cells to an implanted medical product in order to avoid the growth into or clogging of lumens/flexible tubes.

Another object of the present invention is to prevent the adhesion of an implanted medical product to the surrounding tissue.

A still further object of the present invention is to prevent reactive inflammatory zones in implanted medical products, for example, around the distal shunt end in implantable CSF shunts.

Another object of the present invention is to prevent fibrous encapsulation, which may occur in implanted medical products.

The object is achieved by the creation of an implantable medical product having the features of claim 1, the dependent claims 2 to 11 relating to particular embodiments of the medical product according to the invention.

The present invention relates to an implantable medical product. This implantable medical product has a basic body and an imidazole derivative. The imidazole derivative is in the form of its free base rather than the conjugated acid, and especially not in a protonated form. The imidazole derivative is present in a layer provided on the surface of the basic body, said surface being a polymeric surface.

In one embodiment, the imidazole derivative is present as the sole active ingredient in the superficial polymer layer of the basic body.

In particular, the surface of the implantable medical product according to the invention is completely covered by the layer comprising the imidazole derivative.

The medical product according to the invention has antithrombogenic, antiproliferative, anti-inflammatory or antiadhesive effects, or combinations thereof.

Within the meaning of this application, "antithrombogenic" means that an at least reduced thrombogenicity is achieved.

In one embodiment, the imidazole derivative forms the layer surrounding the imidazole derivative, or it is in a molecular-dispersed form in a support material and at the same time forms the outer layer.

In another embodiment, the imidazole derivative is clotrimazole or miconazole.

In another embodiment, the basic body comprises a plastic material, a ceramic, a metal, a metal alloy, a composite material, or combinations thereof.

According to the invention, basic bodies comprising a plastic material, a ceramic, a metal, a metal alloy, a composite material, or combinations thereof are used that are covered, in particular, partially or completely covered, with polymer.

The medical product according to the invention is, in particular, an implantable medical product in which the basic body is a polyurethane, a silicone, a polyamide, a polyethylene terephthalate, a polytetrafluoroethylene, a polyethylene, a biodegradable polymer, a chromium-nickel steel, a cobalt alloy, a titanium alloy, a hydroxyapatite derivative, or combinations thereof.

Examples of biodegradable polymers include polylactides, polyglycolides, polycaprolactone, polyethylene glycol, and combinations thereof.

Another embodiment of the medical product according to the invention has a layer containing the imidazole derivative in a thickness of up to 5 μm, especially up to 2 μm, for example, from 5 to 100 nm. The lower limit for the thickness of the layer containing the imidazole derivative depends on the field of application of the implantable medical product, and can be determined by the skilled person by means of the field of application.

In particular, an implantable medical product comprising antibiotics, especially fusidic acid or rifampicin, antiseptics, such as octenidine, corticosteroids, such as dexamethasone or combinations thereof, is suitable.

In an embodiment according to the invention with the lipophilic imidazole derivative covering the surface, the wetting angle of contact of the surface as measured as a static water contact angle using a Kruess goniometer is more than 80°, preferably 90°-110°.

A water contact angle within the meaning of this application is respectively stated as a static water contact angle. It is determined using a Kruess goniometer (DSA100-M, Kruess GmbH, Hamburg, Germany). Thus, five water drops (aqua dest., 10 µl) are added to each of N=3 material samples, and the corresponding contact angle is measured.

In another embodiment, the keeping quality of the implantable medical product when stored under standard conditions is at least 6 months, preferably at least 12 months, more preferably at least 24 months, most preferably at least 24-36 months.

"Standard conditions" means a temperature of 293.15 K and a pressure of 101.3 kPa (1013 mbar).

In particular, the implantable medical product according to the invention is a catheter, for example, an intravasal catheter.

The implantable medical product according to the invention may be, in particular, a medical product selected from the group consisting of stents, orthopedic, neurological, cardiological or ophthalmological implants, devices for treating parodontose, such as local drug carriers for periodontal pockets, intubators, intraocular lenses, medicament carriers for the topical subgingival application of antimicrobial substances, tracheostoma cannulas, pleura catheters, pleural drainages, pacemaker electrodes, cochlear implant electrodes, silicone shunts, silicone catheters, glaucoma drain devices, polyurethane catheters.

The invention also relates to a process for preparing an implantable medical product, comprising the steps of
  a) providing a medical product basic body;
  b) contacting said medical product basic body with an imidazole derivative;
  c) rinsing, spraying or laminating the medical product;
further optionally comprising the steps of
  d) drying the medical product;
  e) sterilizing the medical product using ethylene oxide and/or by means of gamma radiation.

In another embodiment, the process for preparing an implantable medical product also comprises the incorporation of a further antimicrobial substance into the polymeric basic body.

Thus, a medical product basic body is contacted with an imidazole derivative to form a medical product comprising the basic body and the imidazole derivative. Finally, the medical product is rinsed to remove undesirable residues.

In a particular embodiment, the thus prepared medical product is further dried before being sterilized. In a particular embodiment, the surface homogeneity is improved by said drying, especially drying in a drying cabinet, and the associated initial melting of the miconazole base. The sterilization may be effected by means of ethylene oxide or gamma radiation, especially gamma radiation of 25 kJ/kg (kGray).

Also an embodiment according to the invention is the implantable medical product obtainable by the described process, having antithrombogenic, antiproliferative, antiadhesive and/or anti-inflammatory effects, comprising a basic body and an imidazole derivative in the form of its free base as the sole active substance in a layer for coating a medical product.

Further, the use of the imidazole derivative in the form of its free base for coating implantable medical products is an embodiment according to the invention.

Thus, the imidazole derivative is used in the form of its free base, i.e., non-protonated. An implantable medical product contains a layer comprising the imidazole derivative.

BRIEF DESCRIPTION OF THE FIGURES

FIG. 1 shows an antimicrobial inhibition halo of an intraocular lens containing miconazole/fusidic acid against S. epidermidis RP62A on an MH (Müller-Hinton) plate.

Many implantable materials are recognized as foreign by the body's own immune system, resulting in rejection, loosening, thrombosis, infection or exuberant encapsulation with immigration of undesirable cell populations. Thrombosis, rejection responses and infection of an implant are pathophysiologically associated. Septic phlebitis or endocarditis is associated with the deposition of fibrin, fibronectin and platelet complexes. Especially recently developed drugcontaining implant surfaces exhibit an altered bio and hemocompatibility. This is particularly the case if the coating or modification was effected using relatively toxic substances, such as chlorohexidine, TDMAC (tridodecylmethylammonium chloride), high silver concentrations and benzalkonium Chloride, which have membrane-disrupting effects. However, impregnation with antibiotics whose systemic intravenous application is associated with high thrombophlebitis rates may also adversely affect hemocompatibility.

Methods for optimizing the surfaces of medical products range from the development of novel surfaces, smooth surfaces, biologized surfaces through the development of novel, more tolerable materials to the equipment with potent locally released medicaments. Drawbacks of the previous methods include the high cost of development, a lack of stability of the active substances in endogenous fluids, or a lack of clinical effectiveness, or undesirable side effects. Heparin coatings result in immune thrombocytopenias, acetylic acid results in immune phenomena and in part irreversible side effects.

Surprisingly, these side effects could be avoided at least in part by the medical products according to the invention.

Thus, it has been found that by creating a clearly more lipophilic implant surface by the surface deposition of the almost water-insoluble, very lipophilic imidazole derivatives in the form of their free bases, an anti-adhesive surface supporting the antiproliferative pharmacological effect of the imidazoles can additionally be created. The surface lipophilicity is determined using a water drop on the surface (sessile drop method), through whose wetting angle of contact the wetting behavior, which depends on the surface energy, is determined. Angles clearly smaller than 80° (e.g., in medical thermoplastic polyurethanes) are considered rather more hydrophilic, leading to a facilitated adhesion of endogenous cells, which is subsumed as biocompatible in science. Thus, for example, the wetting angle of contact with polyurethanes decreases in the course of the implantation time by $H_2O$ diffusing into initially swollen hydrophilic microdomains close to the surface. This hydrophilization of the polyurethane surface that depends on the implantation time can be reduced by the molecular-dispersed embedding of miconazole base into these microdomains, thus making cell adhesion more difficult.

Antimicrobial substances, such as antibiotics, can interfere with the coagulation system, both in the plasmatic components of the coagulation system and in platelet activation/aggregation (FAC-Fortschritte der antimikrobiellen Chemotherapie, Antibiotikatherapie and Blutgerinnung, 3-3, Futuramed Verlag 1984). Systemically applied beta-lactam antibiotics reduce the formation of vitamin-K-dependent coagulation factors by destroying the vitamin-Kforming intestinal flora and/or inhibiting vitamin-K epoxide hydrolase (cephalosporins) with subsequent hypoprothrombinemia Immune thrombocytopenia occurs primarily after the application of trimethoprim/sulfmethoxazole and other sulfonamide antibiotics, but is also well documented for other antibiotics. In addition, direct inhibition of the platelet function by an interference of the binding of the aggregation agonists (ADP, adrenalin) is described predominantly for penicillins and some cephalosporins. Such interferences are very rare, because the systemic antibiotic dosages are usually by far not sufficient for a reproducible anticoagulant effect, and such side effects may only occur in disposed patients with existing previous damage in the coagulation system.

There are only a few contradictory pieces of information relating to the side effects with respect to the coagulation system of antimycotics. Miconazole and other antimycotic substances of the imidazole series, such as clotrimazole, can selectively inhibit the synthesis of thromboxane A2 in platelets (Köfeler et al. 2000). Helmeste et al. 1998 could show that miconazole and other imidazole derivatives inhibit cytochrome P450 and consequently inhibit the serotonine uptake into platelets. The aggregation of thrombocytes was examined by three working groups, wherein Steinhilber et al. 1990 and Ishikawa et al. could show inhibiting effects from a concentration of $3 \times 10^{-5}$ M (about 100 µg/ml). In a work by Needleman, it has been found that although the thromboxane synthesis was inhibited, the platelet function was not adversely affected (Needleman et al., Application of imidazole as a selective inhibitor of thromboxane synthetase in human platelets Proc. Natl. Acad. Sci. USA, Vol. 74, No. 4, pp. 1716-1720, 1977; Steinhilber D, Jaschonek K, Knospe J, Morof O, Roth H J. Effects of novel antifungal azole derivatives on the 5-lipoxygenase and cyclooxygenase pathway. Arzneimittelforschung. 1990; 40(11): 1260-3). These findings are overall contradictory and therefore were not further prosecuted scientifically, because potentially aggregation-inhibiting effects of high systemic imidazole concentrations could not be reproducibly achieved in vivo.

Surprisingly, the present invention successfully and reproducibly produces antithrombogenic, antiproliferative and antiadhesive properties in accordingly coated medical products by using imidazole derivatives in the form of their free base, especially the free base of miconazole. It is assumed that this is achieved by the production of high local concentrations of the imidazole derivative close to the surface, without being legally bound in any way by this theory.

Inflammatory processes, iatrogenic or caused by an implant, result in impaired wound healing and failure of the implant. Imidazoles, such as miconazole, show contradictory effects with respect to inflammation: if administered epicutaneously in the form of an ointment in high local concentrations, they may inhibit leukotriene synthesis and possibly influence inflammatory processes of the skin. On a bacterially infected skin, imidazole ointments show partially anti-inflammatory clinical effects (Mertens R L, Morias J, Verhamme G. A double-blind study comparing Daktacort, miconazole and hydrocortisone in inflammatory skin infections. Dermatologica. 1976; 153(4): 228-35), possibly by the reduction of the inflammation-inducing pathogenic bacteria; in contrast, in the tissue and pleura, pro-inflammatory effects with mast cell depletion could be shown (Hanada S, Sugawara S H, Sertié JA. Miconazole as inflammatory agent. II: Time course of pleurisy and drug interference. Gen Pharmacol. 1998; 30(5): 791-4). Inhibition of leukotriene synthesis is possible from concentrations around 100 µg/ml, which cannot be achieved by systemic application. The anti-inflammatory effects are dependent on the AUC (area under the curve) above concentrations of 100 µg/ml, and by far less permanent than those of acetylsalicylic acid, which acts antithrombogenically and antiphlogistically in systemically reachable concentrations, however.

In a long series of loading and release experiments, it has surprisingly been found that reproducible effects inhibiting leukotriene synthesis were achieved at very high local concentrations of miconazole base through specifically designed drug delivery systems. However, clearly higher concentrations, which might be toxic, are avoided by limiting the water solubility of the imidazole derivative base, preferably the almost water-insoluble miconazole base, and the thus minimized local release rate.

Imidazoles, such as miconazole, are weak bases, are processed as salts into ointments or intravenous formulations, and are hardly soluble in water. Solubilizers, such as the toxical Cremophor, are employed for systemic administration for improving water solubility.

Surprisingly, the low water solubility, which is basically disadvantageous, is utilized in the present invention in such a way that, on the one hand, the almost insoluble miconazole base is used instead of the hardly water-soluble miconazole nitrate (as a dispersion suspended in Cremophor), which leads to very low concentrations because of a limited solubility, but long release phases of the active substance close to the surface with concentrations of >100 mg/ml in the medical products according to the invention. Thus, on the one hand, the local toxicity of imidazole close to the surface is controlled and at the same time, the surface tension is reduced if the imidazole wets the whole surface in the form of a fine hydrophobic film. The low surface tension results in a lower adhesion of fibrinogen, platelets and other tissue cells, and thus in a lower rate of deposition thrombi and less overgrowth by fibroblasts.

It is suspected that an effect of a broader, more stable Nernst layer, the so-called stagnant layer, is achieved in addition by the use of the extremely hardly soluble variants of the imidazoles, whereby essentially higher drug concentrations (>100 µg/ml) are achieved in the microenvironment of an implant surface, i.e., at a distance of up to 1-2 µm. All in all, this leads to a stronger effect directly at the surface of an implant, and to no systemic effect. In addition, the water insolubility or lipophilicity results in a stronger passive diffusion through the cell walls/cell membranes into the interior of the cell of adhering platelets, fibroblasts, endothelial cells, or microorganisms.

The combination partners of imidazoles may be further anti-infective agents, such as particular antibiotics, which are suitable for local use and exhibit a synergistic antimicrobial spectrum, or also antiproliferative drugs.

According to the invention, it could be shown in vitro by stationary bacterial inoculums and in passaging experiments that particular combinations surprisingly act synergistically on particular nutrient media, and in addition make the development of resistance improbable. Examples of such combinations include miconazole with free fusidic acid, miconazole with octenidine, and miconazole with rifampicin.

If a combination of the imidazole derivative with a second antimicrobial substance is present in a molecular dispersed distribution under the imidazole derivate base layer, for example, in a polymeric support material, then said second substance, if lipophilic enough, can diffuse through the superficial imidazole derivate layer. In the combination of miconazole with rifampicin, wherein miconazole is in excess, especially in fourfold excess, the resistance development of rifampicin is clearly reduced.

The invention is explained by the following Examples.

EXAMPLE 1: PROCESS FOR PREPARING A MICONAZOLE LAYER ON A POLYURETHANE FILM a) A polyurethane film (pellethane, 2×2 cm, thickness 1 mm) was placed at 20° C. into a solution of 3% by weight rifampicin and 5% by weight miconazole nitrate in ethyl acetate, withdrawn, rinsed with ethanol, which was evaporated under vacuum for 24 hours. Subsequently, the impregnated pellethane film was immersed into a solution of miconazole base (3% by weight) in ethyl acetate for 5 s, slowly withdrawn and, after drying, immersed into a solution of miconazole base (10% by weight) in ethanol for 5 s, and slowly withdrawn again. This procedure was repeated three times.

b) Pellethane polyurethane catheters were placed into a solution of 1% by weight rifampicin and 7% by weight miconazole nitrate in ethyl acetate at 50° C. for 30 min, withdrawn, rinsed with ethanol (30° C.), which was evaporated under vacuum for 24 hours. Subsequently, the impregnated pellethane film, which was drug-free at the surface, was immersed into a solution of miconazole base (3% by weight) in ethyl acetate for 5 s, slowly withdrawn and, after drying, immersed into a solution of miconazole base (10% by weight) in ethanol for 5 s, and slowly withdrawn again. This procedure was repeated three times. Subsequently, the catheter was dried at 85° C. for 5 min and later evaporated under vacuum (100 Pa (1 mbar)).

EXAMPLE 2: DETERMINATION OF THE WATER CONTACT ANGLE

A polyurethane film (pellethane, 2×2 cm, thickness 1 mm) was contacted with a solution of miconazole base as in Example 1.

Thereupon, the surface of an untreated pellethane film was compared with that of an impregnated film coated with miconazole on the surface by means of a static water contact angle using a goniometer (DSA100-MK2, Kruess GmbH, Hamburg, Germany). Five drops (10 µl of aqua dest.) are added to each of 3 samples, and the contact angle was measured. The untreated pellethane film had an averaged contact angle of 82.3°, while an averaged contact angle of 98.2° was obtained for the film coated with miconazole base.

EXAMPLE 3: STERILIZABILITY AND STORABILITY

The effect of sterilization on a central vein catheter coated with miconazole base was determined. Thus, the inhibition halos of *S. epidermidis* RP62A against mixtures of miconazole base and rifampicin were determined, wherein non-sterilized samples were compared with samples sterilized with ethylene oxide or by means of gamma radiation at 25 kJ/kg (25 kGray).

In addition, the samples were examined after a period of 1 and 2 years for examining the storability.

The determinations were performed in triplicate.

It could be shown that implants containing imidazole derivatives could be sterilized by means of ethylene oxide or gamma radiation without a significant proportion of the coating being impaired or damaged by the sterilization process. Further, it could be shown that the keeping quality of further medicaments in a polymer was very long with miconazole base, see Table 1.

TABLE 1

| Agar inhibition halos (mm) against *S. epidermidis* RP62A | | | |
|---|---|---|---|
| | new | after 1 year | after 2 years |
| sterilized (ethylene oxide) | 33.6 | 33.2 | 33.0 |
| sterilized (gamma radiation) | 33.3 | 34.0 | 32.6 |
| not sterilized | 34.3 | 35.0 | 33.5 |

EXAMPLE 4: RELEASE BEHAVIOR

Pellethane polyurethane catheters were provided as in Example 1b).

These catheter pieces were examined by means of agar diffusion test on Müller-Hinton (MH) agar against *Candida albicans* and in a release experiment in PBS buffer at RT by means of UV spectroscopy. With *Candida albicans*, the inhibition halos were at 15 mm on day 1 and remained stable at a level of 10-12 mm for 14 days. The release profile of miconazole was characterized by an initial release of 12 mg/l, falling down to a level of 4-5 mg/(l·$cm_{catheter}$) from day 2. This release level was also sufficient for an inhibition of fibroblast proliferation.

EXAMPLE 5: EXAMINATION OF THE EFFECT OF MICONAZOLE COATINGS ON DIFFERENT MEDICAL PRODUCTS a) Antimicrobial and Antiadhesive Ophthalmological Implants (Lenses) with Fusidic Acid/Miconazole Base The combination of miconazole with fusidic acid with a superficially deposited miconazole base resulted in large inhibition halos against staphylococci and *Candida* spp. (FIG. 1).

Because of superficially deposited miconazole base, the lenses were capable of reducing the growth of fibroblasts. The number of adhering fibroblasts (NHDF adult, Promocell, Heidelberg, Germany) was reduced by 50% in a second experiment (examination with an optical microscope).

b) Medicament Support for the Topical Subgingival Application of Antimicrobial Substances.

Miconazole base and octenidine (5% by weight each) were incorporated in silicone threads (polydimethylsiloxanes, 2 mm diameter) by means of swelling in ethyl acetate. Thereafter, the threads were rinsed with ethanol and again with a 10% ethanol-miconazole base solution. The threads were dried and heated at 85° C. for 5 min. These threads were antimicrobially active beyond 4 weeks as detected by means of the antimicrobial inhibition halos>20 mm (*S. epidermidis* RP62A).

c) Tracheostoma Cannula

A silicone-coated tracheostoma cannula was impregnated with a $CH_3Cl$ miconazole octenidine solution (5% by weight each), surface-coated with miconazole base, and it was antimicrobially active against *S. epidermidis* RP62A and *Candida* spp. beyond 4 weeks.

d) Pleura Catheter

A silicone pleura catheter (2 mm diameter) was impregnated with ethyl acetate and miconazole base/octenidine (5% by weight each), additionally surface-coated with miconazole base, and it was antimicrobially active against *S. epidermidis* RP62A and *Candida* spp. beyond 4 weeks.

e) Pacemaker Electrodes

Silicone-coated electrodes were impregnated with ethyl acetate and miconazole base/octenidine (5% by weight each) and were antimicrobially and antiproliferatively active beyond 4 weeks.

f) Cochlea Implant Electrodes

Silicone-coated cochlea implant electrodes were impregnated with $CH_3Cl$ and miconazole base (5% by weight), surface-coated with 5% by weight EtOH/miconazole base solution, dried and weighed. The amount incorporated into the silicone coat was 4%, and the medical product was antimicrobially and antiproliferatively active beyond 4 weeks.

g) Glaucoma Drain Device

A polyurethane glaucoma drain device was impregnated with ethyl acetate and miconazole base (5% by weight), surface-coated with miconazole base, and it contained 4% miconazole and was antimicrobially and antiproliferatively active beyond 4 weeks.

h) Antithrombogenic Polyurethane Catheter

Polyurethane catheters (pellethanes) were swollen in advance in $CHCl_3$ for 20 min, and impregnated with rifampicin and miconazole base dissolved in $CHCl_3$. Finally, the impregnated catheter was rinsed with a 5% alcohol/miconazole base solution, and dried. The rifampicin/miconazole catheter surface-coated with miconazole showed a clearly reduced surface tension (98° water contact angle in contrast to 80° uncoated), and release rates (inhibition halos against *S. epidermidis* RP62A>15 mm) beyond 4 weeks.

i) Stents

PTFE stents (company Gore, Munich, Germany) were impregnated with $CH_3Cl$ and miconazole base and rifampicin (5% by weight each), surface-coated with miconazole base, and sealed, dried and weighed (5% by weight incorporation rate), showing release rates (>15 mm diameter against *S. epidermidis* RP62A) beyond 4 weeks.

EXAMPLE 6: FIBROBLAST ADHESION

Human fibroblasts (NHDF adult, Promocell, Heidelberg, Germany) were cultivated in a medium (72% Dulbecco's modified Eagle's medium (ATCC, Manassas, USA), 18% Medium M199 (Sigma-Aldrich, Steinheim, Germany), 9% fetal calf serum (PAA Laboratories, Pasching, Austria), and 1% penicillin streptomycin (Invitrogen, Karlsruhe, Germany)) at 37° C.

The fibroblasts were detached from the surfaces by using accutase (PAA Laboratories, Pasching, Austria). The cell count was determined by means of a semiquantitative colorimetric alamarBlue assay (Invitrogen, Karlsruhe, Germany). Pellethane films coated with miconazole base were provided according to Example 5h). These films and unmodified pellethane films were placed into fibroblast cultures with about 15,000 cells/ml. The cells were cultured, and the adhering cells detached after 24, 48 and 72 hours, and the cell count was determined photometrically. The fibroblast count at the untreated pellethane increased continuously as compared to the reduced cell count of the modified pellethane film. In the coated film, an initially 50% lower adhesion occurred, which resulted in an 80% reduced fibroblast adhesion after 72 hours of incubation, i.e., the five-fold amount of adhered cells were present on the unmodified film.

EXAMPLE 7: ANTI-INFLAMMATORY EFFECT—PROSTAGLANDIN $E_2$ ($PGE_2$) INHIBITION UNDER LIPOPOLYSACCHARIDE (LPS) STIMULATION

J774A.1 murine macrophages were incubated over night at a density of $10^5$ cells/ml. The cultures obtained were divided. In one group, respectively 0.2 cm thick uncoated pellethane polyurethane catheter pieces were added to 1 ml of culture solution and 0.1 ml LPS (0.1 µg/ml), and incubated over night at 37° C. in 5% $CO_2$/95%, wherein the verum group obtained catheter pieces surface-coated with miconazole base that were provided according to Example 1.

Thereupon, the supernatants were evaluated on $PGE_2$ according to the instructions of the kit manufacturer (ELISA Development Kit, Peprotech, Rocky Hill, USA; $PGE_2$ ELISA Kit, Thermo Scientific, Pierce Biotechnology, USA).

As compared to the control group, the $PGE_2$ excretion in the presence of the catheter pieces coated with miconazole base could be reduced by 30%.

EXAMPLE 8: IN VITRO DETERMINATION OF THE HEMOCOMPATIBILITY WITH (HIGH STRESS) AND WITHOUT (LOW STRESS) FLOW CONTACT

Whole blood with citrate (3.8% by weight) and hirudine (400 ATU/ml) was added to the sample material (30 min, 37° C.). The latter consisted of two groups. Group 1: uncoated pellethane polyurethane catheters; group 2: pellethane polyurethane catheters loaded with rifampicin and miconazole (1.2% by weight, 4% by weight total weight proportions), with a surface coating with miconazole base.

The samples (1 cm length each) were examined in an in vitro system under low and high shear stress conditions with polymer material to blood volume ratios of 1:10 and 1:1, respectively, according to ISO 10993-12 (see Table 2).

Thereupon, the catheters were tested under different conditions with a centrifuge system (Hettich, Tuttlingen, Germany) with respect to low shear stress (PRP (platelet-rich plasma, 150 g=venous environment) and high shear stress (PPP (platelet-poor plasma, 3000 g=arterial environment) for 30 min. Different parameters of hemocompatibility, such as platelet activation, hemolysis, fibrinolysis, fibrin formation, thrombin generation and contact activation, were evaluated with a score system, wherein a score of 0 was the best, and scores of 5 or 10 were the worst evaluation (Seyfert U. T. Hemocompatibility testing. Clinical Laboratory 43: 571-582, 1997).

TABLE 2

Scoring system of hemocompatibility test

| No. | Criterion | Score points, SP |
|---|---|---|
| 1 | platelet activation | 0-10 |
| 2 | contact activation | 0-5 |
| 3 | fibrinogen-fibrin conversion | 0-10 |
| 4 | thrombin generation | 0 |
| 5 | fibrinolysis | 5 |

TABLE 2-continued

Scoring system of hemocompatibility test

| No. | Criterion | Score points, SP |
|---|---|---|
| 6 | complement activation (C5a) | 5 |
| 7 | hemolysis | 0 |
| 8 | proteolysis (elastase) | 0 |
| | Total | 0-65 |

TABLE 3

Results of the in vitro hemocompatibility test

| | 1 | 2 | 3 | 4 | 5 | 6 | 7 | 8 | Total |
|---|---|---|---|---|---|---|---|---|---|
| Control |
| 1:10, low stress | 1 | 3 | 1 | 2 | 0 | 2 (C5a) | 0 | 1 | 10 |
| 1:10, high stress | 8 | 5 | 2 | 1 | 1 | 0 | 0 | 1 | 18 |
| 1:1, low stress | 0 | 5 | 0 | 3 | 0 | 3 (C5a) | 1 | 3 | 14 |
| 1:1, high stress | 8 | 5 | 2 | 3 | 1 | 0 | 0 | 3 | 22 |
| Coated samples |
| 1:10, low stress | 0 | 1 | 2 | 3 | 0 | 1 (C5a) | 5 | 0 | 12 |
| 1:10, high stress | 7 | 5 | 2 | 3 | 0 | 0 | 0 | 0 | 17 |
| 1:1, low stress | 1 | 5 | 0 | 1 | 0 | 1 (C5a) | 0 | 0 | 8 |
| 1:1, high stress | 8 | 5 | 2 | 1 | 0 | 0 | 0 | 1 | 17 |

Thus, the coated polyurethane surfaces show advantages in both the total hemocompatibility value and, in particular, the contact activation at normal dilution (10%), a lower thrombin generation at a low dilution (50%), and a reduced proteolysis.

EXAMPLE 9: RIFAMPICIN RESISTANCE DEVELOPMENT 10 ml tubes with Müller-Hinton broth (MHB) was brought to a concentration of about $10^6$ CPU with 0.01 ml of an overnight culture with *S. epidermidis* RP62A and *S. aureus* ATCC, and provided with the respective MHC of rifampicin and miconazole. An aliquot was taken from the overnight cultures, brought into new MHB tubes (about $10^6$ CPU), and again incubated over night. This was repeated up to 50 times, and the resistant isolates were frozen. Only from the 30th to 40th passage, rifampicin-resistant isolates were found with MHCs of >64 µg/ml, but no miconazole-resistant isolates were found. In a parallel culture of the two strains with a rifampicin-MHC doping, resistance frequencies of $10^{-6}$ were found. Thus, the addition of miconazole to rifampicin prevents a quick formation of rifampicin resistance.

In a single passage test, a concentration of *S. epidermidis* RP62A and *S. aureus* ATCC of $10^{11}$ CFU/ml in MHB was produced, and an aliquot of this suspension was distributed on blood agar plates. The plates respectively contained the MHC of rifampicin and miconazole.

The overnight culture of the plates was then examined for the number of surviving germs, from which the mutation rate was calculated. A rifampicin resistance rate of about $10^{11}$ was calculated. Thus, the addition of miconazole suppresses the development of resistance of staphylococci against rifampicin.

The invention claimed is:

1. An implantable medical product, comprising a basic body having a polymeric surface, with an imidazole derivative and Rifampicin embedded in said polymeric surface, said polymeric surface covered by a layer consisting essentially of miconazole in the form of its free base, said layer displaying an antithrombogenic, antiproliferative, anti-inflammatory or antiadhesive effect, or a combination thereof, wherein miconazole in the form of its free base is an active ingredient in said layer and wherein the miconazole is the only active ingredient in said layer.

2. The implantable medical product according to claim 1, wherein said imidazole derivative comprises miconazole.

3. The implantable medical product according to claim 1, wherein said basic body comprises a plastic material, a ceramic, a metal, a metal alloy, a composite material, or combinations thereof.

4. The implantable medical product according to claim 1, wherein said basic body comprises a polyurethane, a silicone, a polyamide, a polyethylene terephthalate, a polytetrafluoroethylene, a polyethylene, a biodegradable polymer, a chromium-nickel steel, a cobalt alloy, a titanium alloy, a hydroxyapatite derivative, or combinations thereof.

5. The implantable medical product according to claim 1, wherein said layer has a thickness of up to 5 µm.

6. The implantable medical product according to claim 1, wherein the wetting angle of the polymeric surface as measured as a static water contact angle using a Kruess goniometer is more than 80°.

7. The implantable medical product according to claim 1, wherein its keeping quality when stored under standard conditions is at least 6 months.

8. The implantable medical product according to claim 1, wherein said medical product is a catheter.

9. The implantable medical product according to claim 1, wherein said medical product is selected from the group consisting of stents, orthopedic, neurological, cardiological or ophthalmological implants, devices for treating parodontose, local drug carriers for periodontal pockets, intubators, intraocular lenses, medicament carriers for the topical subgingival application of antimicrobial substances, tracheostoma cannulas, pleura catheters, pleural drainages, pacemaker electrodes, cochlear implant electrodes, silicone shunts, silicone catheters, glaucoma drain devices, polyurethane catheters.

10. An implantable medical product having an antithrombogenic, antiproliferative, antiadhesive and anti-inflammatory effect, comprising a basic body having a polymeric surface, with an imidazole derivative and Rifampicin embedded in said polymeric surface, said polymeric surface covered by a layer consisting essentially of miconazole in the form of its free base, wherein miconazole in the form of its free base is an active ingredient in said layer and wherein the miconazole is the only active ingredient in said layer.

11. The implantable medical product of claim 5, wherein said layer has a thickness of up to 2 µm.

12. The implantable medical product of claim 5, wherein said layer has a thickness of up to 100 nm.

13. The implantable medical product according to claim 6, wherein the static water contact angle is 90°-110°.

14. The implantable medical product of claim 7, wherein its keeping quality when stored under standard conditions is at least 12 months.

15. The implantable medical product of claim 8, wherein the catheter is an intravasal catheter.

16. The implantable medical product of claim 1, wherein the imidazole derivative is an imidazole nitrate salt.

* * * * *